United States Patent
Yoon et al.

(10) Patent No.: US 10,201,326 B2
(45) Date of Patent: Feb. 12, 2019

(54) ULTRASONIC DIAGNOSTIC APPARATUS AND METHOD OF OPERATING THE SAME

(71) Applicant: SAMSUNG ELECTRONICS CO., LTD., Suwon-si (KR)

(72) Inventors: Hee-chul Yoon, Seoul (KR);
Hae-kyung Jung, Seongnam-si (KR);
Hyun-taek Lee, Sejong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 140 days.

(21) Appl. No.: 14/311,800

(22) Filed: Jun. 23, 2014

(65) Prior Publication Data
US 2015/0011885 A1 Jan. 8, 2015

(30) Foreign Application Priority Data

Jul. 2, 2013 (KR) .................. 10-2013-0077298

(51) Int. Cl.
*A61B 8/14* (2006.01)
*A61B 8/00* (2006.01)
(Continued)

(52) U.S. Cl.
CPC .......... *A61B 8/14* (2013.01); *A61B 8/08* (2013.01); *A61B 8/0883* (2013.01); *A61B 8/145* (2013.01);
(Continued)

(58) Field of Classification Search
CPC .......... A61B 8/08; A61B 8/0883; A61B 8/14; A61B 8/145; A61B 8/4444; A61B 8/4477;
(Continued)

(56) References Cited

U.S. PATENT DOCUMENTS

| | | | |
|---|---|---|---|
| 4,747,411 A | | 5/1988 | Ledley |
| 5,879,303 A | * | 3/1999 | Averkiou ................. A61B 8/08 |
| | | | 600/447 |

(Continued)

FOREIGN PATENT DOCUMENTS

| | | |
|---|---|---|
| CN | 101032412 A | 9/2007 |
| CN | 101884553 A | 11/2010 |

(Continued)

OTHER PUBLICATIONS

Communication, Issued by the International Searching Authority, Dated Oct. 12, 2014, In counterpart International Application No. PCT/KR2014/005578.

(Continued)

*Primary Examiner* — Mark Remaly
(74) *Attorney, Agent, or Firm* — Sughrue Mion, PLLC

(57) ABSTRACT

Disclosed is a method for operating an ultrasonic diagnostic apparatus. The method includes transmitting separate first and second ultrasonic signals to an object, receiving a first echo signal which corresponds to the first ultrasonic signal and a second echo signal which corresponds to the second ultrasonic signal, separating the received first and second echo signals in order to generate first ultrasonic data which corresponds to the first echo signal and second ultrasonic data which corresponds to the second echo signal, and displaying a first ultrasonic image which is generated based on the first ultrasonic data and a second ultrasonic image which is generated based on the second ultrasonic data. The first ultrasonic image is an ultrasonic image of a first cross-sectional surface of the object, and the second ultrasonic image is an ultrasonic image of a second cross-sectional surface of the object.

10 Claims, 7 Drawing Sheets

(51) Int. Cl.
*A61B 8/08* (2006.01)
*G01S 15/89* (2006.01)
*G01S 7/52* (2006.01)

(52) U.S. Cl.
CPC .......... *A61B 8/4444* (2013.01); *A61B 8/4477* (2013.01); *A61B 8/463* (2013.01); *A61B 8/466* (2013.01); *A61B 8/483* (2013.01); *A61B 8/5207* (2013.01); *A61B 8/5292* (2013.01); *G01S 15/8959* (2013.01); *G01S 15/8993* (2013.01); *A61B 8/4472* (2013.01); *A61B 8/465* (2013.01); *G01S 7/52074* (2013.01); *G01S 15/8954* (2013.01)

(58) Field of Classification Search
CPC ......... A61B 8/463; A61B 8/465; A61B 8/466; A61B 8/483; A61B 8/5207; A61B 8/5292; G01S 15/8954; G01S 15/8959; G01S 15/8993; G01S 7/52074
See application file for complete search history.

(56) References Cited

U.S. PATENT DOCUMENTS

| | | | |
|---|---|---|---|
| 5,895,855 | A | 4/1999 | Ishikawa et al. |
| 6,014,473 | A | 1/2000 | Hossack et al. |
| 6,179,780 | B1 | 1/2001 | Hossack et al. |
| 6,551,246 | B1 * | 4/2003 | Ustuner .............. G01S 7/52026 600/447 |
| 6,796,944 | B2 | 9/2004 | Hall |
| 6,824,517 | B2 | 11/2004 | Salgo et al. |
| 6,896,658 | B2 | 5/2005 | Ji et al. |
| 6,971,992 | B2 | 12/2005 | Cerofolini |
| 7,043,292 | B2 | 5/2006 | Tarjan et al. |
| 7,251,587 | B2 | 7/2007 | Bondarev et al. |
| 8,277,383 | B2 | 10/2012 | Specht |
| 8,657,751 | B2 | 2/2014 | Tanabe |
| 2003/0078497 | A1 | 4/2003 | Ji et al. |
| 2004/0077945 | A1 | 4/2004 | Cerofolini |
| 2005/0251041 | A1 | 11/2005 | Moehring |
| 2009/0275837 | A1 | 11/2009 | Shiina et al. |
| 2010/0049052 | A1 | 2/2010 | Sharf et al. |
| 2010/0286526 | A1 | 11/2010 | Okamura et al. |
| 2011/0270089 | A1 * | 11/2011 | Vezina ............... A61B 5/02028 600/443 |
| 2011/0306885 | A1 | 12/2011 | Specht |
| 2012/0179037 | A1 | 7/2012 | Halmann |
| 2012/0203107 | A1 | 8/2012 | Kim |

FOREIGN PATENT DOCUMENTS

| | | |
|---|---|---|
| CN | 102626324 A | 8/2012 |
| CN | 102670260 A | 9/2012 |
| EP | 1 723 911 A1 | 11/2006 |
| JP | 11-56851 A | 3/1999 |
| JP | 2004-613 A | 1/2004 |
| JP | 3571587 B2 | 9/2004 |
| JP | 2005-137581 A | 6/2005 |
| JP | 2006-204560 A | 8/2006 |
| JP | 2009-284941 A | 12/2009 |
| WO | 2009145239 A1 | 12/2009 |
| WO | 2013/038217 A1 | 3/2013 |

OTHER PUBLICATIONS

Communication dated Jan. 2, 2017 issued by European Patent Office in counterpart European Application No. 14819440.0.

Communication dated Nov. 29, 2016 issued by Japanese Intellectual Property Office in counterpart Japanese Application No. 2016-523641.

Communication issued by the State Intellectual Property Office of P.R. China on Aug. 7, 2017 in counterpart Chinese Patent Application No. 201480047335.7.

* cited by examiner

FIG. 7

|  | COMPARATIVE EXAMPLE 1 | EMBODIMENT | COMPARATIVE EXAMPLE 2 |
|---|---|---|---|
| PHOTOGRAPHING TIME | TAKE LONG | FAST | SOMEWHAT FAST |
| DEGREE OF DEPENDENCE ON OPERATOR | HIGH | LOW | LOW |
| PATIENT VARIATION | HIGH | LOW | SOMEWHAT LOW |
| VOLUME INFORMATION ACQUISITION | DIFFICULT | SOMEWHAT EASY | EASY |
| CROSS-SECTIONAL DIAGNOSIS INFORMATION | MUCH | MUCH | SOMEWHAT LITTLE |
| TIME RESOLUTION | HIGH | HIGH | LOW |
| PROBE WEIGHT | SMALL | LITTLE | LARGE |
| HARDWARE COST | LITTLE | SOMEWHAT HIGH | HIGH |
| SIMULTANEOUS MULTI-PLANE INFORMATION | IMPOSSIBLE | POSSIBLE | IMPOSSIBLE |

ULTRASONIC DIAGNOSTIC APPARATUS AND METHOD OF OPERATING THE SAME

CROSS-REFERENCE TO RELATED APPLICATIONS

This application claims priority from Korean Patent Application No. 10-2013-0077298, filed on Jul. 2, 2013, in the Korean Intellectual Property Office, the disclosure of which is incorporated herein by reference in its entirety.

BACKGROUND

1. Field

One or more exemplary embodiments relate to an ultrasonic diagnostic apparatus and a method of operating the same, and more particularly, to an ultrasonic diagnostic apparatus and a method of operating the same for acquiring a plurality of cross-sectional ultrasonic images of a same object by using a plurality of probes.

2. Description of the Related Art

Ultrasonic diagnostic apparatuses irradiate an ultrasonic signal, which is generated by a transducer of a probe, onto a target object, and receive information which relates to an echo signal reflected from the object, thereby obtaining an image of an internal part of the object. In particular, ultrasonic diagnostic apparatuses are used for the medical purpose of observing the inside of a target object, detecting a foreign material, and assessing an injury. Ultrasonic diagnostic apparatuses have stabilities higher than those of diagnostic apparatuses using X-rays, display an image in real time, and are safe because there is no exposure to radioactivity, and thus may be widely used in conjunction with other image diagnostic apparatuses.

Ultrasonic diagnostic apparatuses include two-dimensional (2D) ultrasonic diagnostic apparatuses for obtaining 2D ultrasonic images and three-dimensional (3D) ultrasonic diagnostic apparatuses for obtaining 3D ultrasonic images.

In the 2D ultrasonic diagnostic apparatuses that capture an image of an object by using one probe, it takes a relatively long time to acquire an ultrasonic image, and it is relatively difficult to acquire volume information. In the 3D ultrasonic diagnostic apparatuses, it is relatively difficult to acquire cross-sectional diagnosis information, and manufacturing costs are high.

SUMMARY

One or more exemplary embodiments include an ultrasonic diagnostic apparatus and a method of operating the same, which acquires a plurality of cross-sectional ultrasonic images of an object by using a plurality of probes, and performs diagnosis on the basis of the obtained plurality of cross-sectional ultrasonic images.

Additional aspects will be set forth in part in the description which follows and, in part, will be apparent from the description, or may be learned by practice of the presented exemplary embodiments.

According to one or more exemplary embodiments, there is provided a method for operating an ultrasonic diagnostic apparatus, including: transmitting a first ultrasonic signal to an object and transmitting a second ultrasonic signal to the object, the second ultrasonic signal being separate from the first ultrasonic signal; receiving a first echo signal which corresponds to the first ultrasonic signal and receiving a second echo signal which corresponds to the second ultrasonic signal; separating the first echo signal from the second echo signal in order to generate first ultrasonic data which corresponds to the first echo signal and second ultrasonic data which corresponds to the second echo signal; and displaying a first ultrasonic image which is generated based on the first ultrasonic data and displaying a second ultrasonic image which is generated based on the second ultrasonic data, wherein the first ultrasonic image includes an ultrasonic image of a first cross-sectional surface of the object, and the second ultrasonic image includes an ultrasonic image of a second cross-sectional surface of the object.

The method may further include generating a first driving signal which corresponds to the first ultrasonic signal and generating a second driving signal which corresponds to the second ultrasonic signal in order to apply the first driving signal to a first probe and in order to apply the second driving signal to a second probe, wherein the first driving signal is separate from the second driving signal.

The transmitting may include transmitting, by the first probe, the first ultrasonic signal to the object, and transmitting, by the second probe, the second ultrasonic signal to the object.

The generating the first ultrasonic data and the second ultrasonic data may include separating the first echo signal from the second echo signal based on at least one characteristic of at least one from among the first and second ultrasonic signals.

The generating the first ultrasonic data and the second ultrasonic data may include separating the first echo signal from the second echo signal by using at least one from among a frequency band division technique and an orthogonal coding excitation technique.

The first ultrasonic signal may include a first frequency band, and the second ultrasonic signal may include a second frequency band which is different from the first frequency band.

Each of the first and second ultrasonic signals may include a respective orthogonal code.

The generating the first ultrasonic data and the second ultrasonic data may include compressing each of the first and second echo signals.

The method may further include displaying a synthesized image which is generated by synthesizing the first ultrasonic image with the second ultrasonic image.

The synthesized image may include a three-dimensional (3D) ultrasonic image of the object.

The method may further include displaying first cross-sectional information which relates to the first ultrasonic image and second cross-sectional information which relates to the second ultrasonic image in the 3D ultrasonic image.

According to one or more exemplary embodiments, there is provided an ultrasonic diagnostic apparatus including: a first probe configured to transmit a first ultrasonic signal to an object; a second probe configured to transmit a second ultrasonic signal to the object, wherein the first ultrasonic signal is separate from the second ultrasonic signal; an ultrasonic receiver configured to receive a first echo signal which corresponds to the first ultrasonic signal and to receive a second echo signal which corresponds to the second ultrasonic signal, and to separate the first echo signal from the second echo signal in order to generate first ultrasonic data which corresponds to the first echo signal and second ultrasonic data which corresponds to the second echo signal; an image generator configured to generate a first ultrasonic image based on the first ultrasonic data, and to generate a second ultrasonic image based on the second ultrasonic data; and a display component configured to display the generated first ultrasonic image and to display the generated second ultrasonic image, wherein the first ultrasonic image includes an ultrasonic image of a first cross-sectional surface of the object, and the second ultrasonic image includes an ultrasonic image of a second cross-sectional surface of the object.

The ultrasonic diagnostic apparatus may further include an ultrasonic transmitter configured to generate a first driving signal which corresponds to the first ultrasonic signal and to generate a second driving signal which corresponds to the second ultrasonic signal, and further configured to apply the first driving signal to the first probe and to apply the second driving signal to the second probe, wherein the first driving signal is separate from the second driving signal.

The ultrasonic receiver may be further configured to separate the first echo signal from the second echo signal based on at least one characteristic of at least one from among the first and second ultrasonic signals.

The ultrasonic receiver may be further configured to separate the first echo signal from the second echo signal by using at least one from among a frequency band division technique and an orthogonal coding excitation technique.

The ultrasonic receiver may be further configured to compress each of the first and second echo signals.

The display component may be further configured to display a synthesized image which is generated by synthesizing the first ultrasonic image with the second ultrasonic image.

The display component may be further configured to display first cross-sectional information which relates to the first ultrasonic image and second cross-sectional information which relates to the second ultrasonic image in the 3D ultrasonic image.

BRIEF DESCRIPTION OF THE DRAWINGS

These and/or other aspects will become apparent and more readily appreciated from the following description of exemplary embodiments, taken in conjunction with the accompanying drawings of which:

FIGS. 4, 5, 6, and 7 are diagrams which illustrate the method for operating the ultrasonic diagnostic apparatus, according to the exemplary embodiment of FIG. 3.

DETAILED DESCRIPTION

Figure 1:
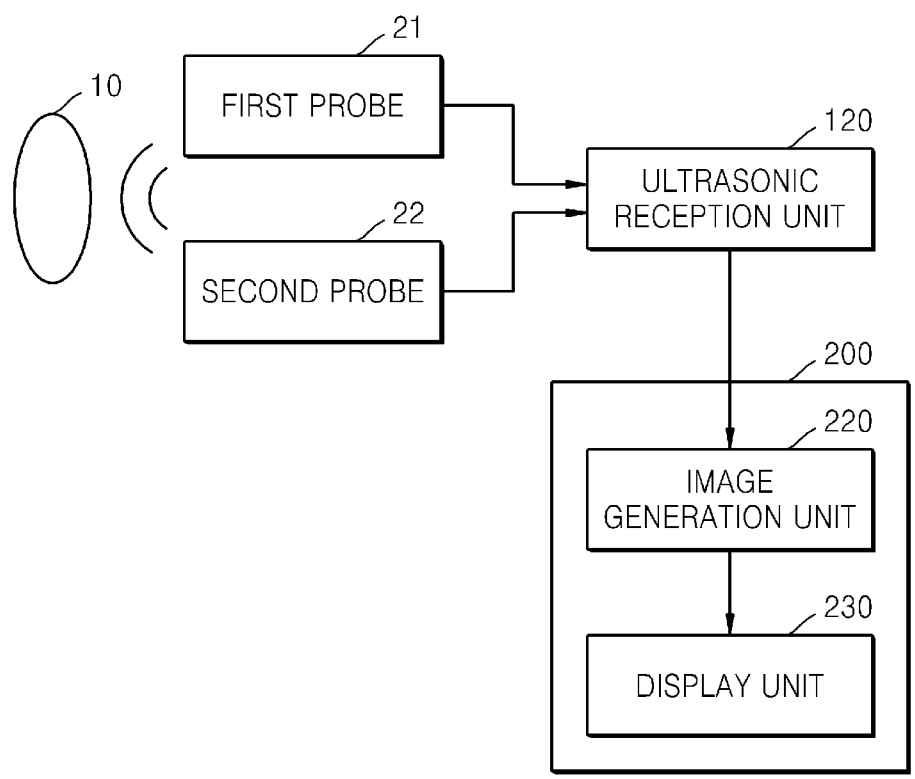
FIG. 1 is a block diagram which illustrates a configuration of an ultrasonic diagnostic apparatus, according to an exemplary embodiment.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, the exemplary embodiments are merely described below, by referring to the figures, in order to explain aspects of the present disclosure.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description. Thus, the terms used herein have to be defined based on the meaning of the terms together with the description throughout the specification.

Also, when a part "includes" or "comprises" an element, unless there is a particular description contrary thereto, the part may further include other elements, not excluding the other elements. Moreover, each of terms such as " . . . unit" and "module" described in specification denotes an element for performing at least one function or operation, and may be implemented in hardware, software or a combination of hardware and software.

The term "ultrasonic image" used herein denotes an image of an object which is acquired by using an ultrasonic wave. Also, the term "object" used herein may include a person, an animal, a part of the person, or a part of the animal. For example, an object may include an organ, such as, for example, a liver, a heart, a womb, a brain, breasts, an abdomen, or the like, or a blood vessel. Also, the term "object" may include a phantom. The phantom denotes a material having a volume that is very close to a density and effective atomic number of an organism, and may include a spherical phantom having a characteristic similar to a physical body.

Moreover, the ultrasonic image may be implemented in various ways. For example, the ultrasonic image may include at least one of an amplitude (A) mode image, a brightness (B) mode image, a color (C) mode image, and a Doppler (D) mode image. Also, according to an exemplary embodiment, the ultrasonic image may include a two-dimensional (2D) image and/or a three-dimensional (3D) image.

Moreover, the term "user" as used herein may refer to a medical expert, and may include any one or more of a doctor, a nurse, a medical technologist, a medical image expert, or the like, or may include an engineer who repairs a medical apparatus. However, the user is not limited thereto.

The present inventive concept will now be described more fully with reference to the accompanying drawings, in which exemplary embodiments are shown. The present inventive concept may, however, be embodied in many different forms and should not be construed as being limited to the exemplary embodiments set forth herein; rather, these exemplary embodiments are provided so that this disclosure will be thorough and complete, and will fully convey the concept to those of ordinary skill in the art. In the following description, well-known functions or constructions are not described in detail since they would obscure the present disclosure with unnecessary detail. Throughout the specification, like reference numerals in the drawings denote like elements.

FIG. 1 is a block diagram which illustrates a configuration of an ultrasonic diagnostic apparatus 1000, according to an exemplary embodiment.

Referring to FIG. 1, the ultrasonic diagnostic apparatus 1000 may include a first probe 21, a second probe 22, an ultrasonic reception unit (also referred to herein as an "ultrasonic receiver") 120, and an image processor 200. Further, the image processor 200 may include an image generation unit (also referred to herein as an "image generator") 220 and a display unit (also referred to herein as a "display device" or a "display component") 230.

A probe according to an exemplary embodiment may be provided in plurality. In FIG. 1, for convenience of description, first and second probes 21 and 22, namely, only two probes, are illustrated, but the exemplary embodiments are not limited thereto.

The plurality of probes, including the first and second probes 21 and 22, may be implemented as a same type, or may be implemented as different types, depending on positions where the probes are respectively used.

Moreover, one or both of the first and second probes 21 and 22 may be implemented as flexible probes which include a flexible material. When a probe is implemented as a flexible probe, a user may easily dispose the probe in a bent area.

Moreover, one or both of the first and second probes 21 and 22 may be configured as wireless probes. When the first and second probes 21 and 22 are configured as wireless probes, the first and second probes 21 and 22 may include a plurality of transducers, and depending on an implementation type, the first and second probes 21 and 22 may include some or all of elements of the ultrasonic reception unit 120.

Each of the first and second probes 21 and 22 may transmit a respective ultrasonic signal to an object 10, and receive a respective echo signal which is reflected from the object 10. In this aspect, the first probe may transmit a first ultrasonic signal, and the second probe may transmit a second ultrasonic signal.

Here, first and second ultrasonic signals may be separate signals. For example, the first and second ultrasonic signals may be signals having different frequency bands.

Alternatively, the first and second ultrasonic signals may be signals composed of codes which are orthogonal to each other. For example, the first and second ultrasonic signals may be signals which are composed of a chirp code which is designed to have orthogonal properties, or may be signals which are composed of a Golay code which is designed to have orthogonal properties. However, the first and second ultrasonic signals are not limited thereto, and in addition, the first and second ultrasonic signals may be signals which are composed of known codes which are orthogonal to each other.

The ultrasonic reception unit 120, according to an exemplary embodiment, may receive a first echo signal which corresponds to the first ultrasonic signal and a second echo signal which corresponds to the second ultrasonic signal. Here, the first echo signal is a signal which is received by the first probe 21, and the second echo signal is a signal which is received by the second probe 22.

The ultrasonic reception unit 120 may include first and second ultrasonic receivers. A signal acquired from the first probe 21 may be received by the first ultrasonic receiver, and a signal acquired from the second probe 22 may be received by the second ultrasonic receiver. However, the present exemplary embodiment is not limited thereto.

The ultrasonic reception unit 120, according to an exemplary embodiment, may separate the first echo signal from the second echo signal.

Here, the first and second echo signals are respective signals which respectively correspond to the first and second ultrasonic signals. The first echo signal may include a characteristic of the first ultrasonic signal, and the second echo signal may include a characteristic of the second ultrasonic signal.

Therefore, the ultrasonic reception unit 120 may separate the first and second echo signals based on the characteristic of the first ultrasonic signal and the characteristic of the second ultrasonic signal.

In this case, the ultrasonic reception unit 120 may separate the first and second echo signals by using a frequency band division technique.

For example, when the first ultrasonic signal has a first frequency band and the second ultrasonic signal has a second frequency band, the first echo signal may have the first frequency band, and the second echo signal may have the second frequency band.

Therefore, the ultrasonic reception unit 120 may separate the first and second echo signals on the basis of a frequency band characteristic of the first ultrasonic signal and a frequency band characteristic of the second ultrasonic signal.

Moreover, the ultrasonic reception unit 120 may separate the first and second echo signals by using an orthogonal coding excitation technique.

For example, when the first ultrasonic signal is a signal which is composed of a first chirp code and the second ultrasonic signal is a signal which is composed of a second chirp code which is orthogonal to the first chirp code, the first echo signal may include a characteristic of the first chirp code, and the second echo signal may include a characteristic of the second chirp code.

Therefore, the ultrasonic reception unit 120 may separate the first and second echo signals based on a frequency band characteristic of the characteristic of the first chirp code and the characteristic of the second chirp code.

Moreover, the ultrasonic reception unit 120 may generate first ultrasonic data which corresponds to the separated first echo signal, and generate second ultrasonic data which corresponds to the separated second echo signal.

The image generation unit 220, according to an exemplary embodiment, may generate a first ultrasonic image based on the first ultrasonic data, and generate a second ultrasonic image based on the second ultrasonic data.

Here, the first ultrasonic image may include an ultrasonic image of a first cross-sectional surface of the object 10, and the second ultrasonic image may include an ultrasonic image of a second cross-sectional surface of the object. The first cross-sectional surface and the second cross-sectional surface may be cross-sectional surfaces which are inclined at different respective angles with respect to a vertical plane.

The display unit 230, according to an exemplary embodiment, may display either or both of the first and second ultrasonic images. Also, the display unit 230 may further display a synthesized image which is generated by synthesizing the first ultrasonic image with the second ultrasonic image. Here, the synthesized image may include a 3D ultrasonic image.

Figure 2:
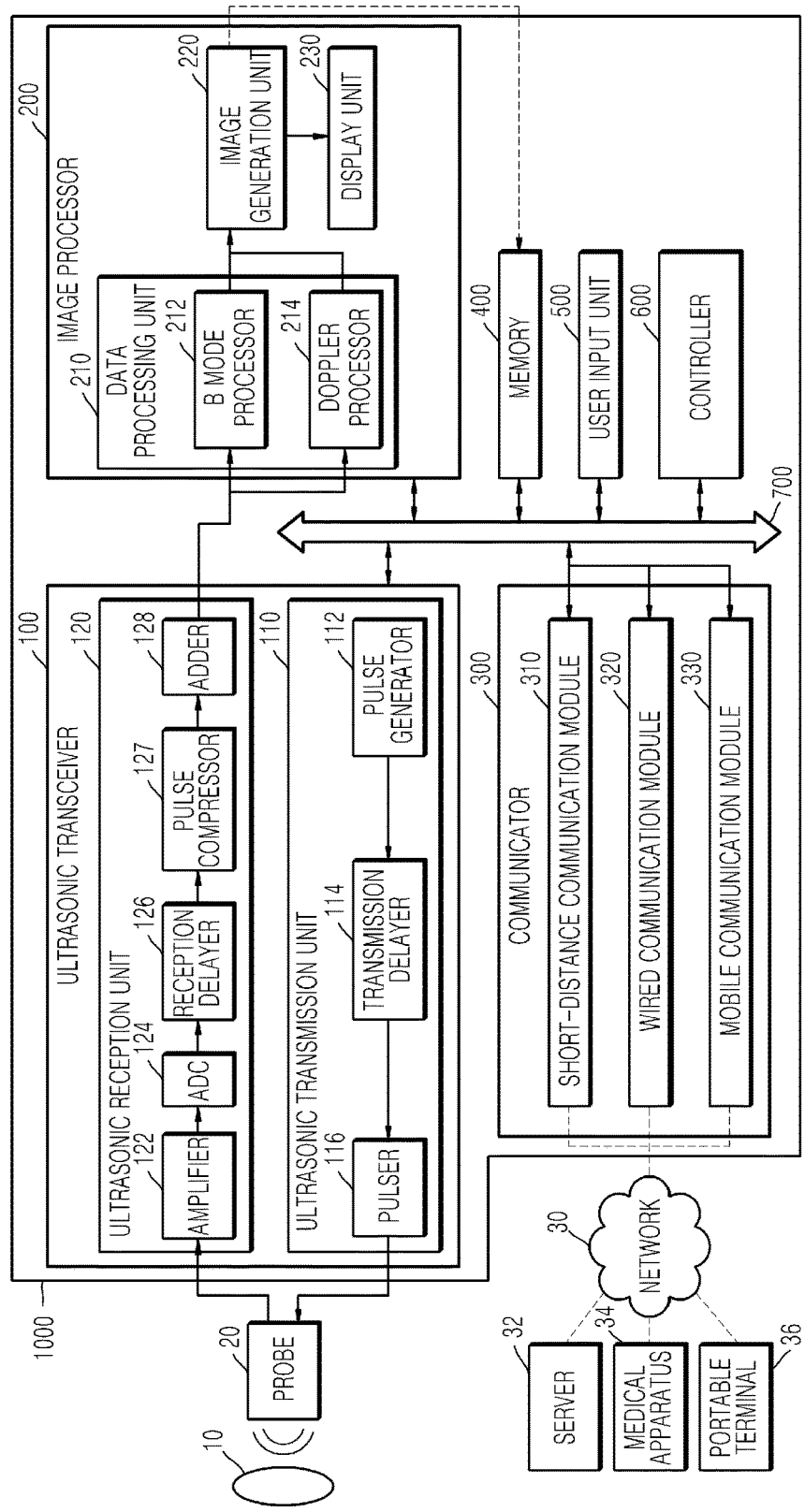
FIG. 2 is a block diagram which illustrates a configuration of an ultrasonic diagnostic apparatus, according to an exemplary embodiment.

FIG. 2 is a block diagram which illustrates a configuration of an ultrasonic diagnostic apparatus 1000, according to an exemplary embodiment.

Referring to FIG. 2, the ultrasonic diagnostic apparatus 1000 according to an exemplary embodiment includes a probe 20, an ultrasonic transceiver 100, an image processor 200, a communicator 300, a memory 400, a user input unit 500, and a controller 600. The above-described elements may be connected to each other via a bus 700.

The ultrasonic diagnostic apparatus 1000 may be implemented as a portable type as well as a card type. Examples of the portable diagnostic apparatuses may include picture archiving and communication system (PACS) viewers, smartphones, laptop computers, personal digital assistants (PDAs), tablet personal computers (PCs), and/or any other suitable device, but are not limited thereto.

The ultrasonic diagnostic apparatus 1000, according to an exemplary embodiment, may include a plurality of the probes 20. Each of the plurality of probes 20 transmits a respective ultrasonic signal to an object 10 based on a respective driving signal which is applied from the ultrasonic transceiver 100, and receives a respective echo signal which is reflected from the object 10. Each of the probes 20 includes a plurality of transducers, which vibrate based on the applied driving signal in order to generate an ultrasonic wave that contains sound energy. Also, the probes 20 may be connected to a body of the ultrasonic diagnostic apparatus 1000 in a wired or wireless manner.

An ultrasonic transmission unit (also referred to herein as an "ultrasonic transmitter") 110 supplies the driving signal to the probe 20, and includes a pulse generator 112, a transmission delayer 114, and a pulser 116. The pulse generator 112 generates a pulse which is used to generate a transmission ultrasonic wave based on a pulse repetition frequency (PRF).

According to an exemplary embodiment, the ultrasonic transmission unit 110 may be provided in plurality. For example, when the probe is provided as a plurality of N probes, the ultrasonic diagnostic apparatus 1000 may include a corresponding number (i.e., N) of ultrasonic transmission units.

Moreover, as described above with respect to FIG. 1, when the ultrasonic diagnostic apparatus 1000 includes the first and second probes 21 and 22, the ultrasonic diagnostic apparatus 1000 may include first and second pulse generators. The first pulse generator may generate a first pulse, which corresponds to a first driving signal, which is applied to the first probe 21. The second pulse generator may generate a second pulse, which corresponds to a second driving signal, which is applied to the second probe 22. Here, the first and second pulses are separate pulses, and may be pulses which do not cause interference therebetween.

The transmission delayer 114 applies a delay time, used to determine a transmission directionality, to the pulse. A plurality of the pulses with the delay time applied thereto correspond to a plurality of piezoelectric vibrators which are included in the probe, respectively. The pulser 116 applies the driving signal (or a driving pulse) to the probe 20 at a timing which corresponds to each of the pulses with the delay time applied thereto.

Here, the driving signal may include the first and second driving signals, and the ultrasonic transmission unit 110, according to an exemplary embodiment, may apply the first and second driving signals to the first and second probes 21 and 22, respectively.

The first probe 21 may transmit the first ultrasonic signal, which corresponds to the applied first driving signal, to the object 10, and the second probe 22 may transmit the second ultrasonic signal, which corresponds to the applied second driving signal, to the object 10.

The ultrasonic reception unit 120 processes the echo signal received from the probe 20 in order to generate ultrasonic data, and includes an amplifier 122, an analog-to-digital converter (ADC) 124, a reception delayer 126, and an adder 128. The amplifier 122 amplifies the echo signal for each channel, and the ADC 124 converts the amplified echo signal from analog to digital. The reception delayer 126 applies a delay time, used to determine a reception directionality, to the converted digital echo signal, and the adder 128 adds a plurality of the echo signals processed by the reception delayer 126 in order to generate the ultrasonic data.

According to an exemplary embodiment, the ultrasonic diagnostic apparatus 1000 may include a plurality of the ultrasonic reception units. For example, when the probe is provided as a plurality of N probes, the ultrasonic diagnostic apparatus 1000 may include a corresponding number (i.e., N) of ultrasonic reception units, which may receive respective echo signals from the plurality of probes.

Moreover, according to an exemplary embodiment, the ultrasonic reception unit 120 may further include a pulse compressor 127. The pulse compressor 127 may compress either or both of the separated first and second ultrasonic signals.

When a long-duration signal having a low voltage is used as an ultrasonic signal, the pulse compressor 127 may perform a pulse compression on an echo signal which corresponds to the ultrasonic signal. Therefore, the ultrasonic diagnostic apparatus 1000 may acquire an ultrasonic image which has a resolution similar to that of a short transmission signal (which has a high peak voltage) being used.

For example, when each of the first and second ultrasonic signals includes a long code string, such as, for example, a chirp code, the pulse compressor 127 may perform pulse compression on each of the received first and second echo signals, and thus, the resolution of an ultrasonic image can be maintained.

The image processor 200 performs a scan conversion on the ultrasonic data which is generated by the ultrasonic transceiver 100 in order to generate and display an ultrasonic image.

According to an exemplary embodiment, the image processor 200 may generate the first ultrasonic image by performing a scan conversion on the first ultrasonic data, generate the second ultrasonic image by performing a scan conversion on the second ultrasonic data, and display the first and second ultrasonic images.

The ultrasonic image may display a motion of an object as a Doppler image in addition to a grayscale ultrasonic image that is generated by scanning the object according to any one or more of the A mode, the B mode, and a motion (M) mode. The Doppler image may include a blood Doppler image (also called a color Doppler image) which indicates a flow of blood, a tissue Doppler image which indicates a motion of a tissue, and a spectral Doppler image that displays a moving speed of the object as a waveform.

A B mode processor 212 extracts a B mode component from the ultrasonic data in order to process the B mode component. An image generation unit 220 may generate an ultrasonic image that displays a signal intensity as a brightness, based on the B mode component which is extracted by the B mode processor 212.

Similarly, a Doppler processor 214 may extract a Doppler component from the ultrasonic data, and the image generation unit 220 may generate a Doppler image that displays a motion of an object as a color or a waveform, based on the extracted Doppler component.

The image generation unit 220, according to an exemplary embodiment, may perform a volume rendering operation on volume data in order to generate a 3D ultrasonic image, and may also generate an elastic image that displays a degree of modification (based on a pressure) of an object 10 as an image. Furthermore, the image generation unit 220 may express various pieces of additional information on the ultrasonic image as texts and graphics. The generated ultrasonic image may be stored in a memory 400.

A display unit 230 displays the ultrasonic image which is generated by the image generation unit 220. The display unit 230 may display various pieces of information which are processed by the ultrasonic diagnostic apparatus 1000, in addition to the ultrasonic image, on a screen via a graphical user interface (GUI). The ultrasonic diagnostic apparatus 1000 may include two or more display units 230, depending on an implementation type.

The display unit 230 includes at least one of a liquid crystal display (LCD), a thin film transistor-liquid crystal display, an organic light-emitting diode (OLED), a flexible display, a 3D display, and an electrophoretic display.

Moreover, when the display unit 230 and the user input unit 500 are implemented as a touch screen by forming a layer structure, the display unit 230 may be used as an input device that enables information to be input by a user's touch, in addition to an output unit.

The communicator 300 is connected to a network 30 in a wired or wireless manner in order to communicate with an external device or server. The communicator 300 may exchange data with a hospital server and/or a medical apparatus of a hospital which is connected thereto via a medical image information system (e.g., a PACS). Also, the communicator 300 may perform data communication according to the digital imaging and communications in medicine (DICOM) standard.

The communicator 300 may transmit and receive data, such as an ultrasonic image, ultrasonic data, Doppler data, and/or any other suitable type of data which relates to an object, which data is associated with a diagnosis of the object, via the network 30, and may also transmit and receive a medical image captured by a medical apparatus such as, for example, any one or more of a computed tomography (CT) apparatus, a magnetic resonance imaging (MRI) apparatus, and/or an X-ray apparatus. Furthermore, the communicator 300 may receive information which relates to a diagnosis history and/or a treatment schedule of a patient from a server, and use a diagnosis of an object. In addition, the communicator 300 may perform data communication with a portable terminal of a doctor and/or with a portable terminal of a patient, in addition to a server or medical apparatus of a hospital.

The communicator 300 may be connected to the network 30 in a wired or wireless manner, and may exchange data with any one or more of a server 32, a medical apparatus 34, and/or a portable terminal 36. The communicator 300 may include one or more elements that enable communication with an external device, and for example, include a short-distance communication module 310, a wired communication module 320, and a mobile communication module 330.

The short-distance communication module 310 refers to a module configured for short-distance communication within a certain distance. Short-distance communication technology, according to an exemplary embodiment, may include any one or more of wireless LAN, Wi-Fi, Bluetooth, Zigbee, Wi-Fi direct (WFD), ultra wideband (UWB), infrared data association (IrDA), Bluetooth low energy (BLE), and near field communication (NFC), but the short-distance communication technology is not limited thereto.

The wired communication module 320 refers to a module for communication using an electrical signal or an optical signal. Wired communication technology, according to an exemplary embodiment, may include any one or more of a pair cable, a coaxial cable, an optical fiber cable, and/or an Ethernet cable.

The mobile communication module 330 transmits and receives a radio frequency (RF) signal to and from a base station, an external terminal, and a server via a mobile communication network. Here, the RF signal may include any one or more of various types of data based on transmission and reception of a voice call signal, a video call signal, or a letter/multimedia message.

The memory 400 stores various pieces of information which are processed by the ultrasonic diagnostic apparatus 1000. For example, the memory 400 may store medical data, such as input/output ultrasonic data and ultrasonic images, which may be associated with a diagnosis of an object, and may also store an algorithm and/or a program which is executed in the ultrasonic diagnostic apparatus 1000.

The memory 400 may be configured with any one or more of various kinds of storage mediums such as a flash memory, a hard disk, an electrically erasable programmable read only memory (EEPROM), and/or any other suitable type of storage medium. Also, the ultrasonic diagnostic apparatus 1000 may operate a web storage facility and/or a cloud server which performs a storage function of the memory 400 on a network.

The user input unit 500 generates input data based on input which is provided by a user for controlling an operation of the ultrasonic diagnostic apparatus 1000. The user input unit 500 may include any one or more of hardware elements such as a keypad, a mouse, a touch pad, a trackball, and/or a jog switch, but is not limited thereto. As another example, the user input unit 500 may further include any one or more of various sensors such as an electrocardiogram (ECG) measurement module, a breath measurement sensor, a voice recognition sensor, a gesture recognition sensor, a fingerprint recognition sensor, an iris recognition sensor, a depth sensor, a distance sensor, and/or any other suitable type of sensor.

In particular, the user input unit 500 may further include the touch screen in which the touch pad and the display unit 230 form the layer structure.

In this case, the ultrasonic diagnostic apparatus 1000 may display a specific mode ultrasonic image and a control panel for controlling an ultrasonic image on the touch screen. In addition, the ultrasonic diagnostic apparatus 1000 may sense a user's touch gesture for manipulating an ultrasonic image via the touch screen.

The controller 600 controls an overall operation of the ultrasonic diagnostic apparatus 1000. In particular, the controller 600 may control operations with respect to each of the probe 20, the ultrasonic transceiver 100, the image processor 200, the communicator 300, the memory 400, and the user input unit 500 which are illustrated in FIG. 1.

Some or all of the probe 20, the ultrasonic transceiver 100, the image processor 200, the communicator 300, the memory 400, the user input unit 500, and the controller 600 may be operated by a software module, but are not limited thereto. Some of the above-described elements may be operated by a hardware module. Further, at least some of the ultrasonic transceiver 100, the image processor 200, and the communicator 300 may be included in the controller 600, but are not limited to the implementation type.

The block diagram of the ultrasonic diagnostic apparatus 1000 of FIG. 2 is a block diagram according to an exemplary embodiment. The elements of the block diagram may be integrated, added, or omitted, depending on a specification of an actually implemented cache memory system. In particular, depending on the particular case, two or more elements may be integrated into one element, or one element may be subdivided into two or more elements. Further, a function performed by each element is for describing an exemplary embodiment, and each element or a detailed operation thereof does not limit a scope and spirit of the exemplary embodiments.

Figure 3:
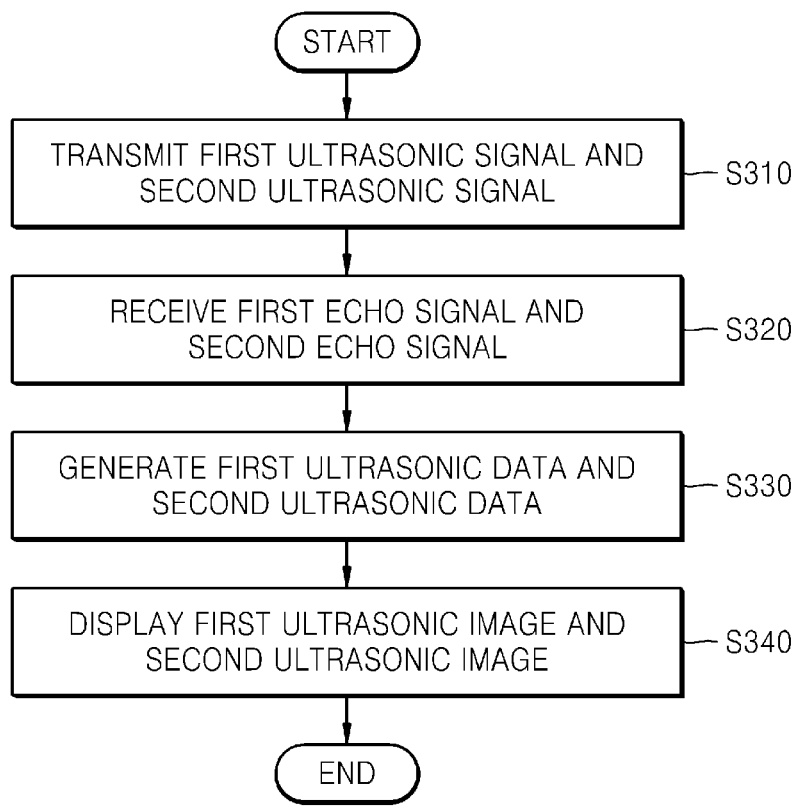
FIG. 3 is a flowchart which illustrates a method for operating an ultrasonic diagnostic apparatus, according to an exemplary embodiment.

FIG. 3 is a flowchart which illustrates a method for operating an ultrasonic diagnostic apparatus, according to an exemplary embodiment, and FIGS. 4, 5, 6, and 7 are diagrams which respectively illustrate the method for operating the ultrasonic diagnostic apparatus according to an exemplary embodiment of FIG. 3.

Referring to FIG. 3, in operation S310, the ultrasonic diagnostic apparatus 1000 transmits each of the separate first and second ultrasonic signals to an object.

Figure 4:
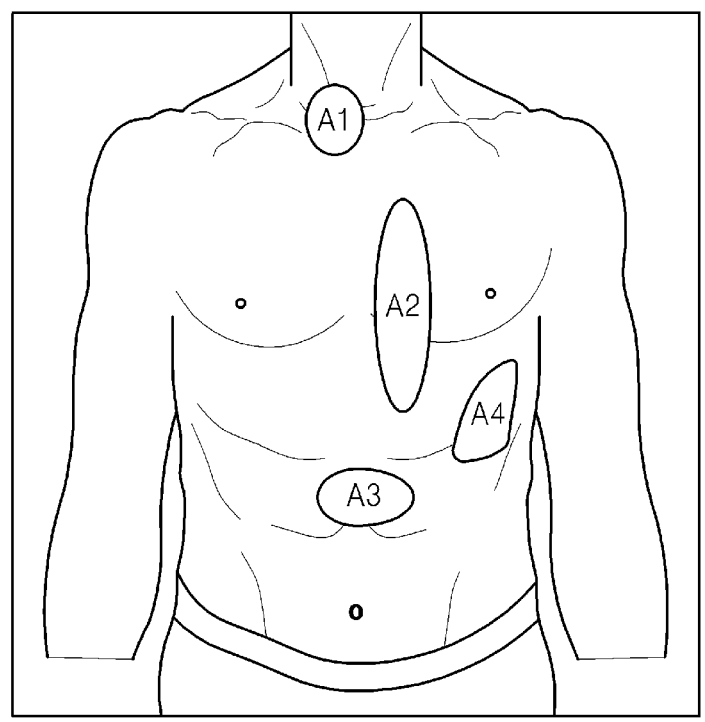

As illustrated in FIG. 4, in order to acquire an ultrasonic image of the object, a user may dispose a plurality of probes, including the first probe 21 and the second probe 22, in one of different first area A1, second area A2, third area A3, and fourth area A4.

In particular, the first, second, third, and fourth areas A1, A2, A3, and A4 may be respective areas for acquiring first, second, third, and fourth cross-sectional images of the object, and may be predetermined areas.

For example, the user may dispose a plurality of probes to have different angles in a right area, a left area, an upper area, and a lower area with respect to a heart, for acquiring first, second, third, and fourth cross-sectional images of the heart.

The ultrasonic diagnostic apparatus 1000 may generate the first and second driving signals, and apply the first and second driving signals to the first and second probes 21 and 22, respectively.

The first probe 21 transmits the first ultrasonic signal, which corresponds to the first driving signal, to the object, and the second probe 21 transmits the second ultrasonic signal, which corresponds to the second driving signal, to the object.

In particular, the first and second ultrasonic signals may include separate signals, and may include signals which do not cause interference therebetween.

For example, the first and second ultrasonic signals may include signals which have different frequency bands.

Alternatively, the first and second ultrasonic signals may include signals which are composed of codes which are orthogonal to each other. For example, the first and second ultrasonic signals may include signals which are respectively composed of a chirp code which is designed to have orthogonal properties, or may include signals which are composed of a Golay code which is designed to have orthogonal properties. However, the first and second ultrasonic signals are not limited thereto, and in addition, the first and second ultrasonic signals may include signals which are composed of known codes which are orthogonal to each other.

Referring again to FIG. 3, in operation S320, the ultrasonic diagnostic apparatus 1000 may receive the first echo signal which corresponds to the first ultrasonic signal, and may receive the second echo signal which corresponds to the second ultrasonic signal.

In particular, the first echo signal is a signal which is received by the first probe 21, and the second echo signal is a signal which is received by the second probe 22.

For example, the first probe 21 may transmit the first ultrasonic signal to the object, receive the first echo signal which is reflected from the object, and transmit the received first echo signal to the ultrasonic reception unit 120. In addition, the second probe 22 may transmit the second ultrasonic signal to the object, receive the second echo signal which is reflected from the object, and transmit the received second echo signal to the ultrasonic reception unit 120.

In operation S330, the ultrasonic diagnostic apparatus 1000 may separate the received first and second echo signals in order to generate the first ultrasonic data, which corresponds to the first echo signal, and to generate the second ultrasonic data, which corresponds to the second echo signal.

In particular, the first and second echo signals are respective signals which respectively correspond to the first and second ultrasonic signals. The first echo signal may include a characteristic of the first ultrasonic signal, and the second echo signal may include a characteristic of the second ultrasonic signal.

Therefore, the ultrasonic reception unit 120 may separate the first echo signal from the second echo signal based on at least one of the characteristic of the first ultrasonic signal and the characteristic of the second ultrasonic signal.

In this case, the ultrasonic reception unit 120 may separate the first and second echo signals by using the frequency band division technique.

For example, when the first ultrasonic signal has a first frequency band and the second ultrasonic signal has a second frequency band, the first echo signal may have the first frequency band, and the second echo signal may have the second frequency band. Therefore, the ultrasonic reception unit 120 may separate the first and second echo signals based on a frequency band characteristic of the first ultrasonic signal and a frequency band characteristic of the second ultrasonic signal.

Moreover, the ultrasonic reception unit 120 may separate the first echo signal from the second echo signal by using the orthogonal coding excitation technique.

For example, when the first ultrasonic signal is a signal which is composed of a first chirp code and the second ultrasonic signal is a signal which is composed of a second chirp code which is orthogonal to the first chirp code, the first echo signal may include a characteristic of the first chirp code, and the second echo signal may include a characteristic of the second chirp code. Therefore, the ultrasonic reception unit 120 may separate the first and second echo signals based on the characteristic of the first chirp code and the characteristic of the second chirp code.

Moreover, the ultrasonic reception unit 120 may generate the first ultrasonic data, which corresponds to the separated first echo signal, and may generate the second ultrasonic data, which corresponds to the separated second echo signal.

In operation S340, the ultrasonic diagnostic apparatus 1000 may display the first ultrasonic image which is generated based on the first ultrasonic data, and may display the second ultrasonic image which is generated based on the second ultrasonic data.

In this case, the ultrasonic diagnostic apparatus 1000 may scan-convert the first ultrasonic data in order to generate the first ultrasonic image, and may scan-convert the second ultrasonic data in order to generate the second ultrasonic image.

In particular, the first ultrasonic image may include an ultrasonic image which is acquired from the first area A1 in which the first probe 21 is located, and the second ultrasonic image may include an ultrasonic image which is acquired from the second area A2 in which the second probe 22 is located.

Moreover, the ultrasonic diagnostic apparatus 1000 may further include third and fourth probes, in addition to the first and second probes 21 and 22. The user may dispose the first, second, third, and fourth probes in the respective first, second, third, and fourth areas A1, A2, A3, and A4, and acquire first ultrasonic image 1410, second ultrasonic image 1420, third ultrasonic image 1430, and fourth ultrasonic image 1440.

Figure 5:
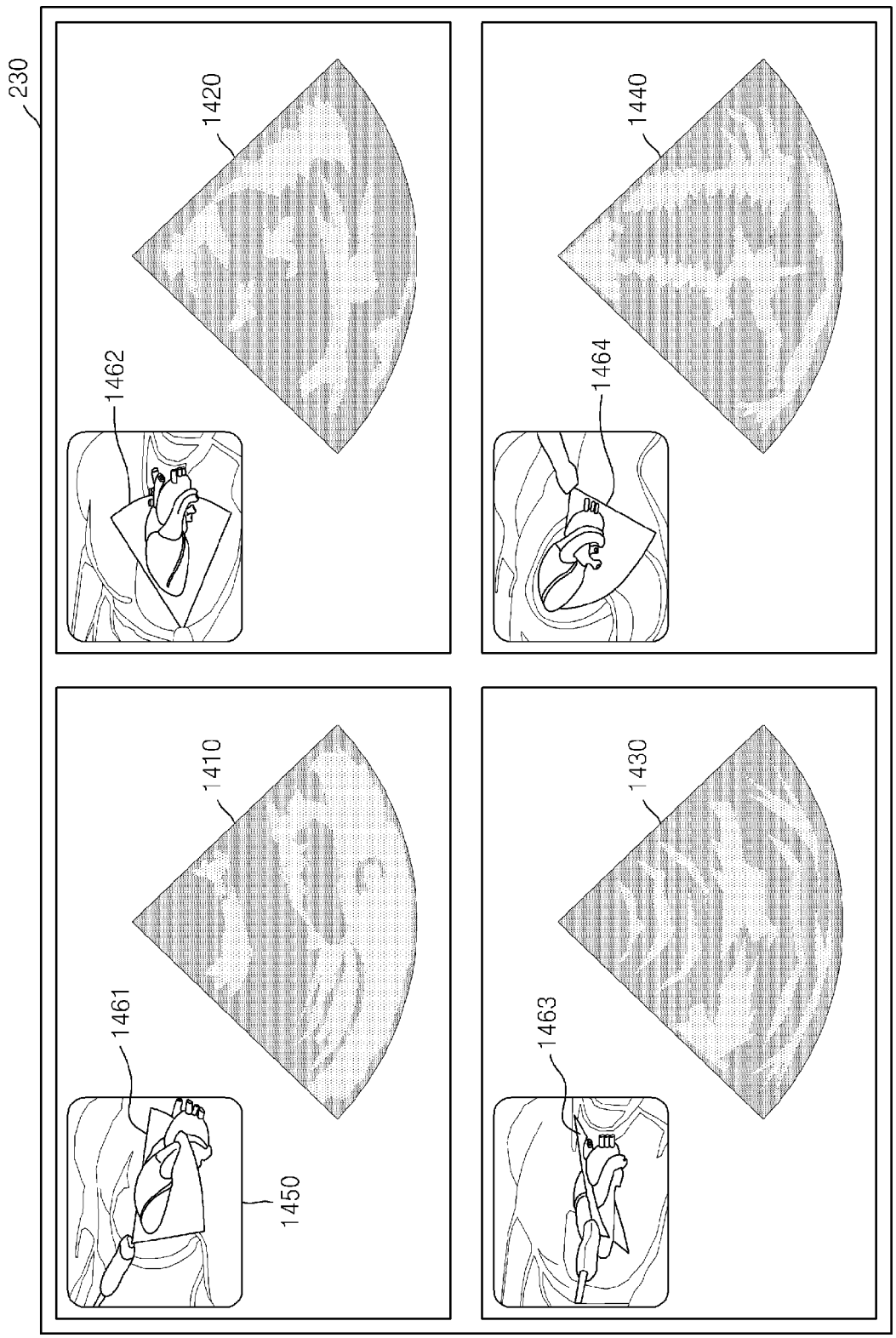

Referring to FIG. 5, the first, second, third, and fourth ultrasonic images 1410, 1420, 1430 and 1440 may be ultrasonic images of a plurality of cross-sectional surfaces of the same object.

For example, when the same object is a heart, the first, second, third, and fourth ultrasonic images 1410, 1420, 1430 and 1440 may be ultrasonic images of different cross-sectional surfaces of the heart which are acquired by the respective probes which are located in the first, second, third, and fourth areas A1, A2, A3, and A4.

For example, the first ultrasonic image 1410 may be an ultrasonic image of a cross-sectional surface which is inclined at a first angle with respect to a vertical plane of the heart, and the second ultrasonic image 1420 may be an ultrasonic image of a cross-sectional surface which is inclined at a second angle with respect to the vertical plane of the heart.

Moreover, the ultrasonic diagnostic apparatus 1000 may display a 3D modeling image 1450 of a combination of component images of the object.

Moreover, the ultrasonic diagnostic apparatus 1000 may display cross-sectional surfaces 1461, 1462, 1463, and 1464, which respectively correspond to the first, second, third, and fourth ultrasonic images 1410, 1420, 1430 and 1440 displayed by the display unit 230, in the 3D modeling image 1450 of the object.

Therefore, the user may adjust an angle and position of the probe 20 while viewing the cross-sectional surface displayed in the 3D remodeling image 1450 of the object, thereby acquiring an appropriate cross-sectional ultrasonic image.

Moreover, the ultrasonic diagnostic apparatus 1000 may move and display the cross-sectional surface, which is displayed in the 3D remodeling image 1450 of the object, in correspondence with a movement of the probe 20

The ultrasonic diagnostic apparatus 1000 may provide a same respective color and a same respective brightness to the same corresponding element of the object as that which is displayed in the first, second, third, and fourth ultrasonic images 1410, 1420, 1430 and 1440.

For example, when each of the first and second ultrasonic images 1410 and 1420 includes first and second blood vessels, the first blood vessels of the first and second ultrasonic images 1410 and 1420 may be displayed in a first color, and the second blood vessels of the first and second ultrasonic images 1410 and 1420 may be displayed in a second color.

Therefore, the user may easily recognize a particular body part in a plurality of cross-sectional images, and may accurately diagnose the particular body part by using the plurality of cross-sectional images.

Figure 6:
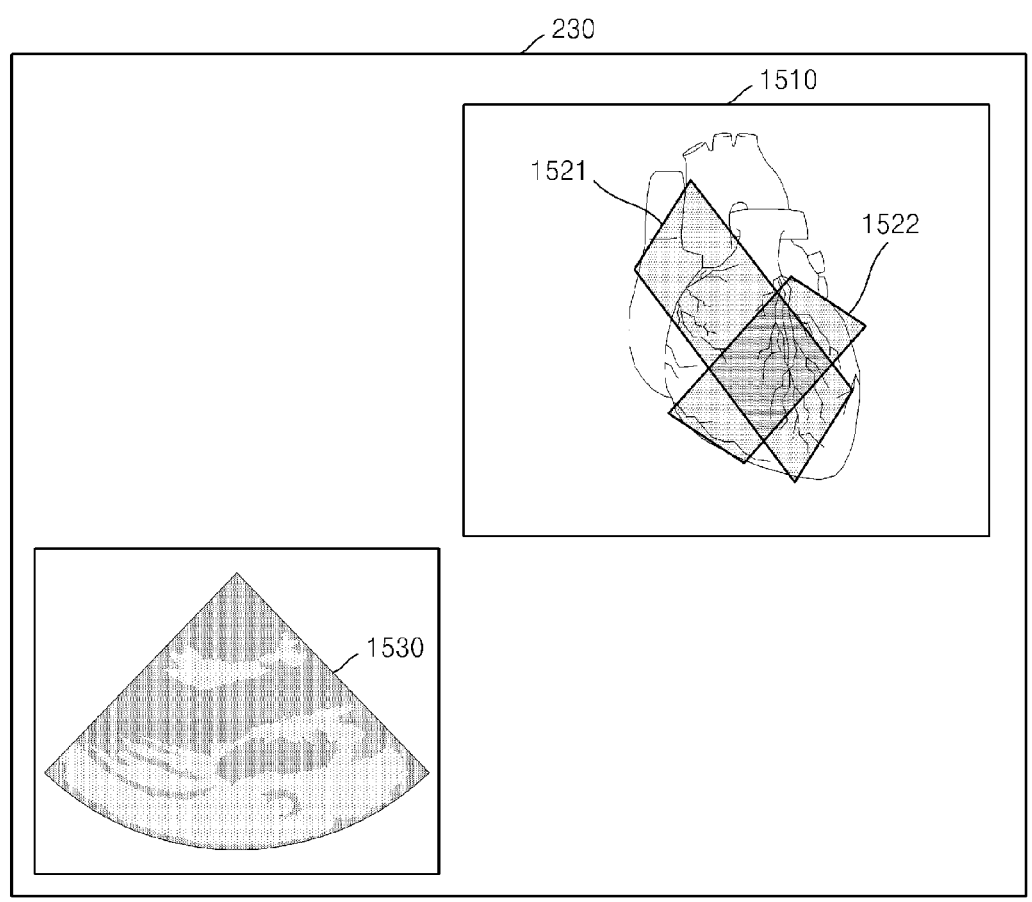

Referring to FIG. 6, the ultrasonic diagnostic apparatus 1000 may display a 3D ultrasonic image 1510 of the object in the display unit 230. In particular, the 3D ultrasonic image 1510 may be a 3D image which is generated via remodeling based on a plurality of ultrasonic data which are respectively acquired from the plurality of probes.

For example, the ultrasonic diagnostic apparatus 1000 may receive echo signals by using each of the first, second, third, and fourth probes, respectively located in the first, second, third, and fourth areas A1, A2, A3, and A4, in order to acquire the first, second, third, and fourth sets of ultrasonic data.

At this time, the ultrasonic diagnostic apparatus 1000 may generate a 2D ultrasonic image and a 3D ultrasonic image by using the first, second, third, and fourth sets of ultrasonic data. For example, the ultrasonic diagnostic apparatus 1000 may generate the 3D ultrasonic image of the object based on a plurality of cross-sectional information (respectively included in each of the first, second, third, and fourth sets of ultrasonic data) which relates to the object.

In this case, as illustrated in FIG. 6, the ultrasonic diagnostic apparatus 1000 may display a plurality of cross-sectional surfaces 1521 and 1522, each of which corresponds to the 2D ultrasonic image, in the 3D ultrasonic image 1510. In FIG. 6, only two cross-sectional surfaces are displayed, but are not limited thereto. For another example, when the number of 2D ultrasonic images is equal to N, the ultrasonic diagnostic apparatus 1000 may display a corresponding number (i.e., N) of cross-sectional surfaces.

When the user selects one cross-sectional surface from among the plurality of cross-sectional surfaces 1521 and 1522 which are displayed in the 3D ultrasonic image 1510, the ultrasonic diagnostic apparatus 1000 may display a 2D ultrasonic image 1530, which corresponds to the selected cross-sectional surface, in the display unit 230.

Moreover, the ultrasonic diagnostic apparatus 1000 may measure the object based on at least one of the 2D ultrasonic image and 3D ultrasonic image of FIGS. 5 and 6.

For example, when the user selects first and second points of the object for a purpose of measuring a distance between the first and second points, the ultrasonic diagnostic apparatus 1000 may display an ultrasonic image which corresponds to a cross-sectional surface which includes both of the first and second points. Therefore, the ultrasonic diagnostic apparatus 1000 can accurately measure the distance between the first and second points based on the displayed ultrasonic image.

FIG. 7 is a diagram that illustrates an exemplary comparison of features of the ultrasonic diagnostic apparatus according to an exemplary embodiment, an ultrasonic diagnostic apparatus of a comparative example 1, and an ultrasonic diagnostic apparatus of a comparative example 2. The ultrasonic diagnostic apparatus of the comparative example 1 is a conventional 2D ultrasonic diagnostic apparatus which includes a single probe, and the ultrasonic diagnostic apparatus of the comparative example 2 is a 3D ultrasonic diagnostic apparatus.

Referring to FIG. 7, in comparison with the ultrasonic diagnostic apparatus of the comparative example 1, the ultrasonic diagnostic apparatus according to an exemplary embodiment may simultaneously acquire ultrasonic images in several directions of an object, and thus reduce a time which would otherwise be required for performing an ultrasonic diagnosis.

Moreover, in the ultrasonic diagnostic apparatus according to an exemplary embodiment, a plurality of probes are respectively located in predetermined areas, and a plurality of ultrasonic images may be acquired. Accordingly, in comparison with the ultrasonic diagnostic apparatus of the comparative example 1, a degree of dependence on a user is reduced.

Moreover, in comparison with the ultrasonic diagnostic apparatus of the comparative example 1, the ultrasonic diagnostic apparatus according to an exemplary embodiment may easily acquire volume information which relates to an object based on simultaneously acquired 2D ultrasonic images in which refer to several directions of application of the ultrasonic diagnostic apparatus according to an exemplary embodiment.

In comparison with the 3D ultrasonic diagnostic apparatus of the comparative example 2, the ultrasonic diagnostic apparatus according to an exemplary embodiment may acquire diagnosis information which relates to a cross-sectional surface of an object, and may simultaneously acquire information which relates to each of a plurality of cross-sectional surfaces.

Moreover, in comparison with the 3D ultrasonic diagnostic apparatus of the comparative example 2, the ultrasonic diagnostic apparatus according to an exemplary embodiment includes a light probe, thus reducing manufacturing costs.

Therefore, when performing ultrasonic diagnosis by using the ultrasonic diagnostic apparatus according to an exemplary embodiment, accurate diagnosis information may be acquired, the manufacturing cost can be reduced, and a user's convenience may be enhanced, in comparison with the conventional 2D ultrasonic diagnostic apparatus and 3D ultrasonic diagnostic apparatus.

The ultrasonic diagnostic apparatus and the method of operating the same according to one or more exemplary embodiments may also be embodied as computer readable codes on a transitory or non-transitory computer readable recording medium. The computer readable recording medium is any data storage device that can store data which may be thereafter read by a computer system. Examples of the computer readable recording medium include read-only memory (ROM), random-access memory (RAM), CD-ROMs, magnetic tapes, floppy disks, and optical data storage devices. The computer readable recording medium can also be distributed over network coupled computer systems so that the computer readable code may be stored and executed in a distributed fashion.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A method for operating an ultrasonic diagnostic apparatus, the method comprising:
    transmitting a first ultrasonic signal comprising a first frequency band to a first region of an object by using a first probe of the ultrasonic diagnostic apparatus, and transmitting a second ultrasonic signal comprising a second frequency band that is different than the first frequency band to a second region of the object by using a second probe of the ultrasonic diagnostic apparatus;
    receiving a first echo signal comprising the first frequency band which corresponds to the first ultrasonic signal and receiving a second echo signal comprising the second frequency band which corresponds to the second ultrasonic signal by using an ultrasonic receiver of the ultrasonic diagnostic apparatus;
    generating, by using the ultrasonic receiver, first ultrasonic data which corresponds to the first echo signal and second ultrasonic data which corresponds to the second echo signal by separating the first echo signal from the second echo signal using a frequency band division technique using the first frequency band of the first ultrasonic signal and the second frequency band of the second ultrasonic signal;
    generating a first ultrasonic image that corresponds to a first cross-sectional surface of the object by scan-converting the first ultrasonic data and generating a second ultrasonic image that corresponds to a second cross-sectional surface of the object by scan-converting the second ultrasonic data, by using an image processor of the ultrasonic diagnostic apparatus; and
    displaying, on a display screen of the ultrasonic diagnostic apparatus, the first ultrasonic image and the second ultrasonic image.

2. The method of claim 1, further comprising generating a first driving signal which corresponds to the first ultrasonic signal and generating a second driving signal which corresponds to the second ultrasonic signal in order to apply the first driving signal to a first probe and in order to apply the second driving signal to a second probe by using an ultrasonic transmitter of the diagnostic apparatus,
    wherein the first driving signal is separate from the second driving signal.

3. The method of claim 1, wherein the generating the first ultrasonic data and the second ultrasonic data includes separating the first echo signal from the second echo signal based on at least one characteristic of at least one from among the first and second ultrasonic signals.

4. The method of claim 1, wherein the generating the first ultrasonic data and the second ultrasonic data further includes separating the first echo signal from the second echo signal by using an orthogonal coding excitation technique.

5. The method of claim 4, wherein each of the first and second ultrasonic signals includes a respective orthogonal code.

6. The method of claim 1, wherein the generating the first ultrasonic data and the second ultrasonic data includes compressing each of the first and second echo signals.

7. The method of claim 1, further comprising displaying, on the display screen, a synthesized image which is generated by synthesizing the first ultrasonic image with the second ultrasonic image.

8. The method of claim 7, wherein the synthesized image includes a three-dimensional (3D) ultrasonic image of the object.

9. A non-transitory computer-readable storage medium storing a program for executing the method of claim 1 in a computer.

10. The method of claim 8, further comprising displaying first cross-sectional information which relates to the first ultrasonic image and second cross-sectional information which relates to the second ultrasonic image in the 3D ultrasonic image.

* * * * *